United States Patent
Lipp et al.

(10) Patent No.: US 9,539,211 B2
(45) Date of Patent: Jan. 10, 2017

(54) ULTRA LOW DENSITY PULMONARY POWDERS

(71) Applicant: Civitas Therapeutics, Inc., Chelsea, MA (US)

(72) Inventors: Michael M. Lipp, Framingham, MA (US); Richard P. Batycky, Newton, MA (US)

(73) Assignee: Civitas Therapeutics, Inc., Chelsea, MA (US)

( * ) Notice: Subject to any disclaimer, the term of this patent is extended or adjusted under 35 U.S.C. 154(b) by 0 days.

(21) Appl. No.: 14/707,071

(22) Filed: May 8, 2015

(65) Prior Publication Data

US 2015/0342885 A1 Dec. 3, 2015

Related U.S. Application Data

(63) Continuation of application No. PCT/US2013/069107, filed on Nov. 8, 2013.

(60) Provisional application No. 61/724,781, filed on Nov. 9, 2012, provisional application No. 61/884,319, filed on Sep. 30, 2013, provisional application No. 61/884,315, filed on Sep. 30, 2013, provisional application No. 61/884,436, filed on Sep. 30, 2013.

(51) Int. Cl.
*A61K 9/14* (2006.01)
*A61K 9/00* (2006.01)
*A61K 31/198* (2006.01)

(52) U.S. Cl.
CPC ............. *A61K 9/145* (2013.01); *A61K 9/0075* (2013.01); *A61K 31/198* (2013.01)

(58) Field of Classification Search
None
See application file for complete search history.

(56) References Cited

U.S. PATENT DOCUMENTS

| | | | |
|---|---|---|---|
| 2,540,059 A | 1/1951 | Stirn et al. |
| 3,656,518 A | 4/1972 | Aronson |
| 3,847,191 A | 11/1974 | Aronson |
| 4,509,568 A | 4/1985 | Kawaguchi et al. |
| 5,756,123 A | 5/1998 | Yamamoto |
| 5,855,913 A | 1/1999 | Hanes et al. |
| 5,874,064 A | 2/1999 | Edwards et al. |
| 5,985,309 A | 11/1999 | Edwards et al. |
| 6,136,295 A | 10/2000 | Edwards et al. |
| RE37,053 E | 2/2001 | Hanes et al. |
| 6,254,854 B1 | 7/2001 | Edwards et al. |
| 6,399,102 B1 | 6/2002 | Edwards et al. |
| 6,436,443 B2 | 8/2002 | Edwards et al. |
| 6,447,752 B2 | 9/2002 | Edwards et al. |
| 6,447,753 B2 | 9/2002 | Edwards et al. |
| 6,503,480 B1 | 1/2003 | Edwards et al. |
| 6,514,482 B1 | 2/2003 | Bartus et al. |
| 6,531,153 B2 | 3/2003 | Seth |
| 6,613,308 B2 | 9/2003 | Bartus et al. |
| 6,635,283 B2 | 10/2003 | Edwards et al. |
| 6,652,837 B1 | 11/2003 | Edwards et al. |
| 6,732,732 B2 | 5/2004 | Edwards et al. |
| 6,740,310 B2 | 5/2004 | Edwards et al. |
| 6,848,197 B2 | 2/2005 | Chen et al. |
| 6,858,199 B1 | 2/2005 | Edwards et al. |
| 6,921,528 B2 | 7/2005 | Edwards et al. |
| 6,932,984 B1 | 8/2005 | Babtsov et al. |
| 6,942,868 B2 | 9/2005 | Edwards et al. |
| 6,977,087 B2 | 12/2005 | Edwards et al. |
| 6,979,437 B2 | 12/2005 | Bartus et al. |
| 7,008,644 B2 | 3/2006 | Batycky et al. |
| 7,048,908 B2 | 5/2006 | Basu et al. |
| 7,052,678 B2 | 5/2006 | Vanbever et al. |
| 7,146,978 B2 | 12/2006 | Edwards et al. |
| 7,182,961 B2 | 2/2007 | Batycky et al. |
| 7,252,840 B1 | 8/2007 | Batycky et al. |
| 7,278,425 B2 | 10/2007 | Edwards et al. |
| 7,384,649 B2 | 6/2008 | Batycky et al. |
| 7,435,408 B2 | 10/2008 | Edwards et al. |
| 7,469,488 B2 | 12/2008 | Chen et al. |
| 7,556,798 B2 | 7/2009 | Edwards et al. |
| 7,628,977 B2 | 12/2009 | Edwards et al. |
| 7,754,242 B2 | 7/2010 | Basu et al. |
| 7,879,358 B2 | 2/2011 | Jackson et al. |
| 7,947,742 B2 | 5/2011 | Batycky et al. |
| 7,954,491 B2 | 6/2011 | Hrkach |

(Continued)

FOREIGN PATENT DOCUMENTS

| | | |
|---|---|---|
| EP | 2494962 A2 | 9/2012 |
| GB | 2454480 A | 5/2009 |
| WO | 9740819 A1 | 11/1997 |
| WO | 0113893 A2 | 3/2001 |
| WO | 0195874 A2 | 12/2001 |
| WO | 02053190 A2 | 7/2002 |
| WO | 02083220 A2 | 10/2002 |
| WO | 02085326 A2 | 10/2002 |
| WO | 03043585 A2 | 5/2003 |
| WO | 03079885 A2 | 10/2003 |

(Continued)

OTHER PUBLICATIONS

Freed, M., et al., "Rapid Levodopa Augmentation Following Inhaled CVT-301 Results in Rapid Improvement in Motor Response When Administered to PD Patients in the OFF State, Neurology," 82(10), Supplement S7.007, abstract.

(Continued)

*Primary Examiner* — Bethany Barham
*Assistant Examiner* — Barbara Frazier
(74) *Attorney, Agent, or Firm* — Elmore Patent Law Group, P.C.; Darlene A. Vanstone; Carolyn S. Elmore

(57) ABSTRACT

The invention provides pharmaceutical compositions for pulmonary delivery comprising particles containing a pharmaceutical agent and having a geometric size of greater than about 5 μm and a tap density of less than about 0.075 g/cm$^3$. The invention also provides methods for delivering the pharmaceutical compositions of the invention to the respiratory tract of a patient.

**9 Claims, No Dr

(56) References Cited

U.S. PATENT DOCUMENTS

| | | |
|---|---|---|
| 8,231,375 B2 | 7/2012 | Remon et al. |
| 8,268,358 B2 | 9/2012 | Batycky et al. |
| RE43,711 E | 10/2012 | Jackson et al. |
| 8,399,513 B2 | 3/2013 | Karaborni et al. |
| 8,404,276 B2 | 3/2013 | Jackson et al. |
| 8,415,397 B2 | 4/2013 | Batycky et al. |
| 8,454,939 B2 | 6/2013 | Hrkach |
| 8,496,002 B2 | 7/2013 | Ellwanger et al. |
| 8,545,878 B1 | 10/2013 | Kee et al. |
| 8,586,093 B2 | 11/2013 | Jackson et al. |
| 8,614,255 B2 | 12/2013 | Blizzard et al. |
| 8,628,754 B2 | 1/2014 | Edwards et al. |
| 8,685,442 B1 | 4/2014 | Batycky et al. |
| 8,747,813 B2 | 6/2014 | Batycky et al. |
| 8,821,928 B2 | 9/2014 | Hemmingsen et al. |
| 8,887,715 B2 | 11/2014 | Hrkach |
| 8,945,612 B2 | 2/2015 | Kee et al. |
| 9,155,699 B2 | 10/2015 | Jackson et al. |
| 9,295,661 B2 | 3/2016 | Batycky et al. |
| 9,393,210 B2 | 7/2016 | Kee et al. |
| 2002/0035993 A1 | 3/2002 | Edwards et al. |
| 2002/0058009 A1 | 5/2002 | Bartus et al. |
| 2003/0072799 A1 | 4/2003 | Sowden et al. |
| 2003/0131905 A1 | 7/2003 | Duffield |
| 2003/0180352 A1 | 9/2003 | Patel et al. |
| 2004/0003866 A1 | 1/2004 | Rocchio et al. |
| 2004/0018989 A1 | 1/2004 | Jackson et al. |
| 2004/0028735 A1 | 2/2004 | Kositprapa |
| 2004/0168739 A1 | 9/2004 | Bonney et al. |
| 2004/0265242 A1 | 12/2004 | Bartus et al. |
| 2006/0216345 A1 | 9/2006 | Dhavse et al. |
| 2006/0222699 A1 | 10/2006 | Gilinski |
| 2007/0117788 A1 | 5/2007 | Yeadon |
| 2007/0275060 A1 | 11/2007 | Befumo et al. |
| 2008/0063722 A1 | 3/2008 | Ward et al. |
| 2008/0066741 A1 | 3/2008 | LeMahieu et al. |
| 2008/0230145 A1 | 9/2008 | Schmied et al. |
| 2010/0040691 A1 | 2/2010 | Richards et al. |
| 2010/0074947 A1 | 3/2010 | Brown et al. |
| 2010/0189780 A1 | 7/2010 | Walz et al. |
| 2010/0197565 A1 | 8/2010 | Smutney et al. |
| 2010/0316712 A1 | 12/2010 | Nangia et al. |
| 2010/0330170 A1 | 12/2010 | Gilinski |
| 2011/0123574 A1 | 5/2011 | Basu et al. |
| 2011/0151008 A1 | 6/2011 | Jackson et al. |
| 2011/0268666 A1 | 11/2011 | Friedman et al. |
| 2012/0064126 A1 | 3/2012 | Sung et al. |
| 2012/0164233 A1 | 6/2012 | Bhargava et al. |
| 2013/0287854 A1 | 10/2013 | Morgan et al. |
| 2014/0007874 A1 | 1/2014 | Ellwanger et al. |
| 2014/0088202 A1 | 3/2014 | Cade et al. |
| 2014/0178476 A1 | 6/2014 | Edwards et al. |
| 2014/0193501 A1 | 7/2014 | Bartus et al. |
| 2015/0094378 A1 | 4/2015 | Batycky et al. |
| 2015/0114392 A1 | 4/2015 | Hrkach |
| 2015/0320711 A1 | 11/2015 | Kee et al. |
| 2015/0328175 A1 | 11/2015 | Batycky et al. |
| 2015/0342885 A1 | 12/2015 | Lipp et al. |
| 2015/0342890 A1 | 12/2015 | Penachio et al. |
| 2016/0058727 A1 | 3/2016 | Jackson et al. |
| 2016/0151393 A1 | 6/2016 | Blizzard et al. |

FOREIGN PATENT DOCUMENTS

| | | |
|---|---|---|
| WO | 03079992 A2 | 10/2003 |
| WO | 03080163 A1 | 10/2003 |
| WO | 2004002551 A2 | 1/2004 |
| WO | 2004112702 A2 | 12/2004 |
| WO | 2007092088 A1 | 8/2007 |
| WO | 2007112581 A1 | 10/2007 |
| WO | 2008156586 A2 | 12/2008 |
| WO | 2009026434 A1 | 2/2009 |
| WO | 2012066319 A1 | 5/2012 |
| WO | 2014066206 A1 | 5/2014 |
| WO | 2014074795 A1 | 5/2014 |
| WO | 2014074796 A1 | 5/2014 |
| WO | 2014074797 A1 | 5/2014 |
| WO | 2015163840 A1 | 10/2015 |

OTHER PUBLICATIONS

Okereke, C.S., "Role of Integrative Pharmacokinetic and Pharmacodynamic Optimization Strategy in the Management of Parkinson's Disease Patients Experiencing Motor Fluctuations with Levodopa," J. Pharm., Pharmaceutical Science, 5(2): pp. 146-161 (2002).

Bartus, et al., "A Pulmonary Formulation of L-Dopa Enhances its Effectiveness in a Rat model of Parkinson's Disease," Journal of Pharmacology and Experimental Therapeutics, 310(2):828-835, 2004.

Hardie, et al., "The Pharmacokinetics of Intravenous and Oral Levodopa in Patients with Parkinson's Disease who Exhibit On-Off Fluctuations," British Journal of Clinical Pharmacology, 22:429-436, 1986.

Ku, S., et al., "Performance Qualification of a New Hypromellose Capsule, Part II. Disintegration and Dissolution Comparison Between Two Types of Hypromellose Capsules," Capsugel Library, Retrieved from the internet: http://www.capsugel.com/media/library, retrieved on Jun. 20, 2016.

ULTRA LOW DENSITY PULMONARY POWDERS

RELATED APPLICATIONS

This application is a continuation of PCT/US2013/069107, filed Nov. 8, 2013 which claims the benefit of U.S. Provisional Application No. 61/724,781, filed on Nov. 9, 2012; U.S. Provisional Application No. 61/884,319; U.S. Provisional Application No. 61/884,315; U.S. Provisional Application No. 61/884,436, all filed on Sep. 30, 2013. The entire teachings of the above applications are incorporated herein by reference.

BACKGROUND OF THE INVENTION

Delivering large doses of drug through the pulmonary route is very difficult. Dry powder inhalers offer advantages in delivering high dose drugs. In a dry powder formulation, choosing a formulation with a high percentage of drug and a low percentage of excipient can help delivery high dose drugs, but it can often be difficult to manufacture and use such powders. Applicants have discovered an ultralow density pulmonary dry powder which allows for high doses of the powder to be packaged in a delivery compartment while being released from the inhaler as highly respirable particles.

SUMMARY OF THE INVENTION

The invention provides pharmaceutical compositions for pulmonary delivery comprising particles containing a pharmaceutical agent and having a geometric size of greater than about 5 µm and a tap density of less than about 0.075 g/cm³. The invention also provides methods for delivering the pharmaceutical compositions of the invention to the respiratory tract of a patient. In one embodiment, the pharmaceutical compositions include particles comprising levodopa for pulmonary delivery to the respiratory tract of a patient suffering from Parkinson's disease.

DETAILED DESCRIPTION OF THE INVENTION

In one embodiment, the invention is a pharmaceutical composition for pulmonary delivery comprising particles containing a pharmaceutical agent and having a median geometric size of greater than about 5 microns (µm) and a tap density of less than about 0.075 g/cm³. In one aspect of the invention, the tap density is from about 0.02 to 0.075 g/cm³. In another aspect of the invention, the tap density is from about 0.02 to 0.05 g/cm³. In a further aspect of the invention, the tap density is from about 0.03 to 0.06 g/cm³. In one aspect of the invention, the tap density is from about 0.03 to 0.04 g/cm³. In another aspect of the invention the median geometric size is about 5 µm to 30 µm, 5 µm to 10 µm, 7 µm to 15 µm, or 7 µm to 12 µm.

In another embodiment, the invention is a method of delivering a pharmaceutical agent to the pulmonary system of a patient comprising the steps of:
  providing a powder in a compartment and an inhaler to a patient wherein said powder comprises particles of a pharmaceutical agent;
    dispersing the powder by breath actuation of the patient;
    delivering the particles to the patient's respiratory system;
    wherein upon dispersion of the powder, the particles delivered to the patient's respiratory system have a smaller median geometric diameter than the particles contained in said compartment.

In one aspect of the invention, the powder has a tap density of less than about 0.75 g/cm³, from about 0.02 to 0.075 g/cm³, or from about 0.025 to 0.055 g/cm³.

In one aspect of this invention, an inhaler is a dry powder inhaler. A variety of inhalers can be used including the Aerolizer, Diskus, Flexhaler, Handihaler, Neohaler, Pressair, Rotahaler, Turbohaler, and Twisthaler. Other dry powder inhalers which can be used are described in U.S. Pat. Nos. 6,766,799, 7,278,425 and 8,496,002 each of which are hereby incorporated in by reference for their disclosure relating to the inhalation devices described therein.

In one aspect of the invention, the compartment is a capsule or a blister pack. In one aspect of the invention, the inhaler has a resistance of about 0.05 to about 0.25, about 0.15 to about 0.25, 0.05 to about 0.15, 0.2 to about 0.25, or about 0.2. Resistance as referred herein is measured in: square root of cm $H_2O$/(Liters/minute).

In another aspect of the invention, the powder in said compartment has a median geometric diameter of greater than about 5 µm, of about 5 µm to about 30 µm, of about 5 µm to about 15 µm, or of about 7 µm to about 12 µm. In one specific embodiment, the particles in said compartment have a median geometric diameter of 10-12 µm and the particles delivered to the patient's respiratory tract have a median geometric diameter of 8-9 µm. In another embodiment, the particles delivered to the patient's respiratory tract have a 5% to 20% smaller, 5% to 10% smaller, or 8% to 15% smaller median geometric diameter than the particles in said compartment.

In one embodiment, the invention is a pharmaceutical composition for pulmonary deliver comprising particles of levodopa having a geometric size of greater than about 5 µm and a tap density of less than about 0.075 g/cm³. In one aspect of this invention, the particles comprise a phospholipid. In another aspect of this invention, the particles comprise a salt. In a further aspect of this invention, the particles comprise a surfactant or a polymer.

In one embodiment, particles of this invention have an external surface area of greater than 10 m²/g. In another embodiment, the external surface area is greater than 15 m²/g, greater than 20 m²/g or about 10 m²/g to about 50 m²/g.

In one specific embodiment, the invention is a pharmaceutical composition for pulmonary deliver comprising particles of levodopa having a geometric size of about 8 µm to about 12 µm and a tap density of about 0.025 g/cm³ to about 0.050 g/cm³ and a water content between 1.90 and 2.90 weight percent. This specific invention, in some instances, may be characterized by particles having an aerodynamic diameter of between about 2.5 µm and 5 µm, particles having an external surface area of about 10 m²/g to about 50 m²/g, or said particles further comprising a salt and a phospholipid. In one very specific embodiment, the invention is a pharmaceutical composition for pulmonary delivery comprising particles of levodopa, dipalmitoylphosphatidylcholine and sodium chloride, wherein said particles have a geometric size of about 8 µm to about 12 µm and a tap density of about 0.025 g/cm³ to about 0.050 g/cm³. In an even more specific embodiment, the invention is a pharmaceutical composition for pulmonary delivery comprising particles of levodopa, dipalmitoylphosphatidylcholine (DPPC) and sodium chloride, wherein said particles have a geometric size of about 8 µm to about 12 µm, and a tap density of about 0.025 g/cm³ to about 0.050 g/cm³, an aerodynamic diameter of between about 2.5 µm and 5 µm, and an external surface area of about 10 to about 50 m²/g.

The inhalation powder may contain additional excipients. Examples of excipients include salts such as sodium chloride (NaCl), sodium citrate, sodium lactate, and potassium chloride and phospholipids such as dipalmitoylphosphatidylcholine (DPPC) dilauroylphosphatidylcholine (DLPC), disaturated-phosphatidylcholine (DSPC). In one embodiment, the pharmaceutical composition contains a powder comprising 90% levodopa, 8% dipalmitoylphosphatidylcholine, and 2% sodium chloride as measured by % of dry solids in the powder. In one embodiment the pharmaceutical composition contains an inhalable powder having a dry weight ratio of 90:8:2 of levodopa:DPPC:NaCl. In another embodiment the capsule contains an inhalable powder having a dry weight ratio of 90:5:5 of levodopa:DPPC:NaCl.

Gravimetric analysis, using Cascade impactors, is a method of measuring the size distribution of airborne particles. The Andersen Cascade Impactor (ACI) is an eight-stage impactor that can separate aerosols into nine distinct fractions based on aerodynamic size. The size cutoffs of each stage are dependent upon the flow rate at which the ACI is operated. Preferably the ACI is calibrated at 60 L/min. In one embodiment, a two-stage collapsed ACI is used for particle optimization. The two-stage collapsed ACI consists of stages 0, 2 and F of the eight-stage ACI and allows for the collection of two separate powder fractions. At each stage an aerosol stream passes through the nozzles and impinges upon the surface. Particles in the aerosol stream with a large enough inertia will impact upon the plate. Smaller particles that do not have enough inertia to impact on the plate will remain in the aerosol stream and be carried to the next stage.

The ACI is calibrated so that the fraction of powder that is collected on a first stage is referred to herein as "fine particle fraction" or "FPF". The FPF corresponds to the percentage of particles that have an aerodynamic diameter of less than 5.6 μm. The fraction of powder that passed the first stage of the ACI and is deposited on the collection filter is referred to as "FPF(3.4)". This corresponds to the percentage of particles having an aerodynamic diameter of less than 3.4 μm.

The FPF fraction has been demonstrated to correlate to the fraction of the powder that is deposited in the lungs of the patient, while the FPF(3.4) has been demonstrated to correlate to the fraction of the powder that reaches the deep lung of a patient. In accordance with the invention, the FPF of the inhalable powder of the nominal dose contained in the capsule (i.e., the percentage of particles in the powder contained in the capsule that have an aerodynamic diameter of less than 5.6 μm) is about 40% or more. In one embodiment the FPF of the nominal powder dose of the inhalable powder contained in the capsule is about 50%, 60%, or 70%, or 80%, or 90%. In one embodiment the FPF is about 50% to about 60% of the nominal powder dose of the inhalable powder contained in the inhaler. In one embodiment the FPF is about 55% to about 65% of the nominal powder dose of the inhalable powder contained in the inhaler. In one embodiment the FPF is about 50% to about 70% of the nominal powder dose of the inhalable powder contained in the inhaler. In one embodiment the FPF is about 57% to about 62% of the nominal powder dose of the inhalable powder contained in the inhaler. In one embodiment the FPF is about 50% to about 69% of the nominal powder dose of the inhalable powder contained in the inhaler. In one embodiment the FPF is about 50%, 51%, 52%, 53%, 54%, 55%, 56%, 57%, 58%, 59%, 60%, 61%, 62%, 63%, 64%, or 65% of the nominal powder dose of the inhalable powder contained in the inhaler.

As used herein, the term "nominal powder dose" is the total amount of powder held in the capsule. As used herein, the term "nominal drug dose" is the total amount of drug (e.g. levodopa) contained in the nominal powder dose. The nominal powder dose is related to the nominal drug dose by the load percent of drug in the powder.

In one embodiment, the nominal powder dose is 25-50 mg by dry weight. In a further embodiment, the nominal powder dose is 25-40 mg by dry weight. In a still further embodiment, the nominal powder dose is 30-35 mg by dry weight or 32-38 mg by dry weight.

Another method for measuring the size distribution of airborne particles is the multi-stage liquid impinger (MSLI). The Multi-stage liquid Impinger (MSLI) operates on the same principles as the Anderson Cascade Impactor (ACI), but instead of eight stages there are five in the MSLI. Additionally, instead of each stage consisting of a solid plate, each MSLI stage consists of a methanol-wetted glass frit. The wetted stage is used to prevent bouncing and re-entrainment, which can occur using the ACI. The MSLI is used to provide an indication of the flow rate dependence of the powder. This can be accomplished by operating the MSLI at 30, 60, and 90 L/min and measuring the fraction of the powder collected on stage 1 and the collection filter. If the fractions on each stage remain relatively constant across the different flow rates then the powder is considered to be approaching flow rate independence.

In one embodiment, the inhalable powders of the invention have a tap density of less than about 0.075 $g/cm^3$. For example, the particles have a tap density between 0.02 $g/cm^3$ and 0.075 $g/cm^3$, between 0.02 $g/cm^3$ and 0.05 $g/cm^3$, between 0.03 $g/cm^3$ and 0.06 $g/cm^3$, between 0.03 $g/cm^3$ and 0.04 $g/cm^3$, or less than about 0.05 $g/cm^3$, or a tap density less than about 0.04 $g/cm^3$, a tap density less than about 0.03 $g/cm^3$. Tap density can be measured by using instruments known to those skilled in the art such as the Dual Platform Microprocessor Controlled Tap Density Tester (Vankel, N.C.) or a GEOPYC™ instrument (Micrometrics Instrument Corp., Norcross, Ga., 30093). Tap density is a standard measure of the envelope mass density. Tap density can be determined using the method of USP Bulk Density and Tapped Density, United States Pharmacopia Convention, Rockville, Md., $10^{th}$ Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed. In one embodiment of the invention, the particles have an envelope mass density of less than about 0.4 $g/cm^3$.

The inhalable powder of the invention has a preferred particle size, e.g., a volume median geometric diameter (VMGD) of at least about 1 micron (μm). In one embodiment, the VMGD is greater than 5 μm. In other embodiments, the VMGD is between about 5 μm and 30 μm, between about 5 μm and 10 μm, between about 7 μm and 15 μm and between about 7 μm and 12 μm. The diameter of the spray-dried particles, for example, the VMGD, can be measured using a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

The particles of the inhalable powder of the invention preferably have a "mass median aerodynamic diameter" (MMAD), also referred to herein as "aerodynamic diameter", between about 1 μm and about 5 μm or any subrange encompassed between about 1 μm and about 5 μm. For example, the MMAD is between about 1 μm and about 3 μm, or the MMAD is between about 3 μm and about 5 μm. In one embodiment, the MMAD is between 1.5 μm and 2.5 μm. Experimentally, aerodynamic diameter can be determined by employing a gravitational settling method, whereby the time for an ensemble of powder particles to settle a certain distance is used to infer directly the aerodynamic diameter of the particles. An indirect method for measuring the mass median aerodynamic diameter (MMAD) is the multi-stage liquid impinger (MSLI). The aerodynamic diameter, $d_{aer}$, can be calculated from the equation:

$$d_{aer} = d_g \sqrt{\rho_{tap}}$$

where $d_g$ is the geometric diameter, for example the MMGD, and $\rho$ is the powder density.

Powders for use in capsules of this invention are typically produced by spray drying. In some cases, spray-drying can produce extremely dry particles which may have poor handling properties and may be difficult to compact into a capsule in a dense manner. A nitrogen source with a specified moisture level may be flown over, across, or through the dry powder to add specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

The inhalable powder comprising levodopa, for example, as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics.

If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. If synthetic plastics are used as the capsule material, examples according to the invention may be selected from polyethylene, polycarbonate, polyester, polypropylene and polyethylene terephthalate. In one embodiment, the capsule material further comprises titanium dioxide. In one preferred embodiment the capsule comprises HPMC and titanium dioxide. In one embodiment, the capsule comprises carrageenan. In a further embodiment, the capsule comprises potassium chloride. In a still further embodiment, the capsule comprises, HPMC, carrageenan, potassium chloride, and titanium dioxide. In one embodiment, the capsule size is selected from 000, 00, 0, 1, or 2. In a specific embodiment, the capsule size is 00.

In one specific embodiment, the capsule is a hydroxypropylmethylcellulose (HPMC) capsule. In another specific embodiment, the capsule is a hydroxypropylmethylcellulose size 00 capsule. In one specific embodiment the capsule material comprises HPMC and titanium dioxide and the capsule size is 00.

In one embodiment, a 00 capsule contains between 15 and 50 grams of levodopa by dry weight. In another embodiment, a 00 capsule contains between 20 and 40 grams of levodopa by dry weight. In another embodiment, a 00 capsule contains between 25 and 35 grams of levodopa by dry weight. In another embodiment, a 00 capsule contains about 30, 31, 32, 33, 34, 35, 36, 37, 38, 39, or 40 grams of levodopa by dry weight.

In one aspect of the invention, the powders have low electrostatic charge to enable high dispersion from the capsule.

The capsules of the invention are particularly suitable for use in a dry powder inhaler for the delivery of a dry powder composition comprising levodopa to a patient afflicted with, for example, Parkinson's disease and in need of treatment with levodopa. The patient in need of treatment may require maintenance therapy for Parkinson's disease or rescue therapy for Parkinson's disease such as would be necessary in the case of an acute and/or freezing episode due to Parkinson's disease. In one embodiment, the capsules are used in a dry powder inhaler to deliver an effective amount of the dry powder composition to the patient in a single breath as is described in U.S. Pat. Nos. 6,858,199 and 7,556,798 incorporated herein by reference.

As used herein, the term "effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated. In the case of a dopamine precursor, agonist or combination thereof it is an amount which reduces the Parkinson's symptoms which require therapy. Dosages for a particular patient are described herein and can be determined by one of ordinary skill in the art using conventional considerations, (e.g. by means of an appropriate, conventional pharmacological protocol). For example, effective amounts of oral levodopa range from about 50 milligrams (mg) to about 500 mg. In many instances, a common ongoing (oral) levodopa treatment schedule is 100 mg eight (8) times a day.

The administration of more than one dopamine precursor, agonist or combination thereof, in particular levodopa, carbidopa, apomorphine, and other drugs can be provided, either simultaneously or sequentially in time. Carbidopa or benserazide, for example, is often administered to ensure that peripheral carboxylase activity is completely shut down. Intramuscular, subcutaneous, oral and other administration routes can be employed. In one embodiment, these other agents are delivered to the pulmonary system. These compounds or compositions can be administered before, after or at the same time. In a preferred embodiment, particles that are administered to the respiratory tract include both Levodopa and carbidopa. The term "co-administration" is used herein to mean that the specific dopamine precursor, agonist or combination thereof and/or other compositions are administered at times to treat the episodes, as well as the underlying conditions described herein.

In one embodiment chronic levodopa therapy includes the use of the pharmaceutical compositions described herein in a dry powder inhaler for pulmonary delivery of levodopa combined with oral carbidopa. In another embodiment, pulmonary delivery of levodopa is provided during the episode, while chronic treatment can employ conventional oral administration of levodopa/carbidopa. In a further embodiment chronic levodopa therapy includes the use of the pharmaceutical compositions described herein in a dry powder inhaler for pulmonary delivery of levodopa combined with oral benserazide. In another embodiment, pulmonary delivery of levodopa is provided during the episode, while chronic treatment can employ conventional oral administration of levodopa/benserazide.

The present invention will be further understood by reference to the following non-limiting examples.

EXAMPLES

Example 1

Process One Powder Preparation

Levodopa and DPPC at room temperature for 30 minutes, after which the required amounts of water and ethanol are weighed and transferred to the jacketed aqueous and non-jacketed organic phase feed vessels respectively. The jacket on the aqueous phase vessel is set to 55° C., and the weighed water is allowed to heat up to the 52.5° C., following which the required amount of sodium chloride and L-dopa are added to the aqueous phase vessel and the required amount of DPPC is added to the organic phase vessel, and all of them are allowed to dissolve by stirring. The aqueous feed vessel headspace is purged with nitrogen maintained at 70 scfh.

Spray drying is initiated by starting the drying gas flow (set to 95 kg/hr) and the exhaust, and the heater for the drying gas is set to 125° C. The product filter heater is turned on and set to 60° C., and the liquid skid heater is turned on and set to 55° C. After the spray dryer outlet temperature reaches 80° C., the atomizing gas (set to 22 g/min) and the blank solvents (aqueous flow=28 mL/min and organic flow=42 mL/min) are initiated and allowed to stabilize, and the system is allowed to cool and stabilize to an outlet temperature of 52.5° C. Product filter pulsing is initiated and product filter purge flow is set to 15 scfh. After the system stabilizes at 52.5° C., the liquid skid inlets are switched to feed solvents. Table 1 summarizes the parameters maintained during the entire operation.

TABLE 1

Process parameters for spray drying

| Process Parameters (OC) | Target value |
|---|---|
| Inlet Temperature (° C.) | 125.0 |
| Outlet Temperature (° C.) | 52.5 |
| Drying Gas Rate (kg/hr) | 95.0 |
| Chamber Pressure ("wc) | −2.0 |
| Atomization Gas Flow Rate (g/min) | 22.0 |
| Aqueous Flow (mL/min) | 28.0 |
| Organic flow (mL/min) | 42.0 |
| Product filter purge rate (scfh) | 15.0 |

Spray dried powder is collected every hour and transferred to a larger vessel under controlled conditions of 20° C. and 15% RH. After the feed solvents run out, the liquid skid inlets are switched to blank and allowed to run for about 10 minutes, during which the final powder is collected and combined. After 10 minutes on blank solvent, system shutdown is initiated by turning off the liquid lines, atomization gas, drying gas heater, drying gas inlet and finally the exhaust.

This process results in a powder containing about 3.4% water by weight.

Example 2

Process Two Powder Preparation with Special Drying

Levodopa and DPPC at room temperature for 30 minutes, after which the required amounts of water and ethanol are weighed and transferred to the jacketed aqueous and non-jacketed organic phase feed vessels respectively. The jacket on the aqueous phase vessel is set to 55° C., and the weighed water is allowed to heat up to the 52.5° C., following which the required amount of sodium chloride and L-dopa are added to the aqueous phase vessel and the required amount of DPPC is added to the organic phase vessel, and all of them are allowed to dissolve by stirring. The aqueous feed vessel headspace is purged with nitrogen maintained at 70 scfh.

Spray drying is initiated by starting the drying gas flow (set to 95 kg/hr) and the exhaust, and the heater for the drying gas is set to 125° C. The product filter and the optimized purge gas heaters are turned on and set to 60° C., and the liquid skid heater is turned on and set to 55° C. After the spray dryer outlet temperature reaches 80° C., the atomizing gas (set to 22 g/min), the blank solvents (aqueous flow=28 mL/min and organic flow=42 mL/min), and the optimized drying gas (set at 70 kg/hr) are initiated and allowed to stabilize, and the system is allowed to cool and stabilize to an outlet temperature of 52.5° C. Product filter pulsing is initiated and product filter purge flow is set to 15 scfh. After the system stabilizes at 52.5° C., the liquid skid inlets are switched to feed solvents. Table 2 summarizes the parameters maintained during the entire operation.

TABLE 2

Process parameters for spray drying

| Process Parameters (OC) | Target value |
|---|---|
| Inlet Temperature (° C.) | 125.0 |
| Outlet Temperature (° C.) | 52.5 |
| Drying Gas Rate (kg/hr) | 95.0 |
| Chamber Pressure ("wc) | −2.0 |
| Atomization Gas Flow Rate (g/min) | 22.0 |
| Aqueous Flow (mL/min) | 28.0 |
| Organic flow (mL/min) | 42.0 |
| Optimized drying purge rate (kg/hr) | 70.0 |
| Optimized drying purge temperature (° C.) | 52.5 |
| Product filter purge rate (scfh) | 15.0 |

Spray dried powder is collected every hour and transferred to a larger vessel under controlled conditions of 20° C. and 15% RH. After the feed solvents run out, the liquid skid inlets are switched to blank and allowed to run for about 10 minutes, during which the final powder is collected and combined. After 10 minutes on blank solvent, system shutdown is initiated by turning off the liquid lines, optimized drying gas, atomization gas, drying gas heater, drying gas inlet and finally the exhaust.

This process results in a powder containing about 2.2% water by weight. This reduction in water content by 1% results in a significant improvement in product stability.
Sample 1: Based on bulk powder (pre-filling):
VMGD=10.2 μm; and
Tap density=0.033 g/cm$^3$.

Sample 2: Same but using VMGD measured on filled lot (60031):
VMGD=8.6 µm; and
Tap=0.033 g/cm$^3$.
Sample 1. Emitted powder from a dry powder inhaler with a resistance of 0.2 (28.3 LPM):
VMGD=9.4 µm; and
Tap density=0.048 g/cm$^3$.
Sample 2. Emitted powder from a dry powder inhaler with a resistance of 0.2 ((60 LPM):
VMGD=8.8 µm; and
Tap density=0.042 g/cm$^3$.

The above particles are very low density for pulmonary products. These very low density particles are advantageous for packing into capsules. Because of the low density, these particles can be deaggregated or sheared prior to emission from an inhaler. These deaggregated/sheared particles have good flow properties and expected deposition into the lungs.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A pharmaceutical composition for pulmonary delivery comprising particles of levodopa having:
    a geometric size of about 8 µm to about 12 µm;
    a tap density of about 0.025 g/cm$^3$ to about 0.050 g/cm$^3$;
    a water content between 1.90 and 2.90 weight percent.
2. The pharmaceutical composition of claim 1, wherein said particles comprise a phospholipid.
3. The pharmaceutical composition of claim 1, wherein said particles comprise a salt.
4. The pharmaceutical composition of claim 1, wherein said particles comprise a surfactant.
5. The pharmaceutical composition of claim 1, wherein said particles comprise a polymer.
6. The pharmaceutical composition of claim 1, wherein said particles comprise a sugar.
7. The pharmaceutical composition of claim 1, wherein said particles have an aerodynamic diameter of between about 2.5 µm and 5 µm.
8. The pharmaceutical composition of claim 1, wherein said particles have an external surface area of about 10 m$^2$/g to about 50 m$^2$/g.
9. The pharmaceutical composition of claim 1, wherein said particles further comprise a salt and a phospholipid.

* * * * *